United States Patent
Kaur et al.

(10) Patent No.: US 12,252,576 B2
(45) Date of Patent: Mar. 18, 2025

(54) PROCESS AND CATALYST COMPOSITION FOR PRODUCING LINEAR ALPHA OLEFINS IN HIGH YIELD BY ETHYLENE OLIGOMERIZATION

(71) Applicant: Indian Oil Corporation Limited, Mumbai (IN)

(72) Inventors: Sukhdeep Kaur, Faridabad (IN); Rashmi Rani, Faridabad (IN); Gurmeet Singh, Faridabad (IN); Dheer Singh, Faridabad (IN); Anju Chopra, Faridabad (IN); Gurpreet Singh Kapur, Faridabad (IN); Sankara Sri Venkata Ramakumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 18/058,377

(22) Filed: Nov. 23, 2022

(65) Prior Publication Data
US 2023/0159672 A1    May 25, 2023

(30) Foreign Application Priority Data
Nov. 23, 2021 (IN) .............................. 202121053985

(51) Int. Cl.
| | |
|---|---|
| *C07C 2/32* | (2006.01) |
| *B01J 31/14* | (2006.01) |
| *B01J 31/22* | (2006.01) |
| *C08F 4/52* | (2006.01) |
| *C08F 4/76* | (2006.01) |

(52) U.S. Cl.
CPC ................ *C08F 4/76* (2013.01); *B01J 31/14* (2013.01); *B01J 31/22* (2013.01); *C07C 2/32* (2013.01); *C08F 4/52* (2013.01)

(58) Field of Classification Search
CPC .............. C07C 2/32; B01J 31/14; B01J 31/22
See application file for complete search history.

(56) References Cited

U.S. PATENT DOCUMENTS

| | | |
|---|---|---|
| 4,486,615 A | 12/1984 | Langer, Jr. |
| 4,783,573 A | 11/1988 | Shiraki et al. |
| 5,260,500 A | 11/1993 | Shiraki et al. |
| 5,345,023 A | 9/1994 | Chauvin et al. |
| 8,653,316 B2 | 2/2014 | Aliyev et al. |
| 9,050,587 B2 | 6/2015 | Aliyev et al. |
| 2005/0070425 A1 | 3/2005 | Biagini et al. |
| 2021/0178376 A1* | 6/2021 | Singh ...................... B01J 31/22 |

FOREIGN PATENT DOCUMENTS

| | | |
|---|---|---|
| EP | 0241596 A1 | 10/1987 |
| WO | 2007090412 A2 | 8/2007 |

* cited by examiner

*Primary Examiner* — Caixia Lu
(74) *Attorney, Agent, or Firm* — Workman Nydegger

(57) ABSTRACT

The present disclosure relates to a process for producing linear alpha olefins in high yield carried out by oligomerization of ethylene in the presence of a novel catalyst composition. The catalyst composition includes Zirconium compound, an organoaluminum compound, and at least one Lewis base selected from cyclic and acyclic ethers (i.e., di-n-butyl ether and diethyl ether). The process for oligomerization of ethylene is carried out in an inert organic solvent in the presence of said catalyst composition. The process as disclosed herein provides significantly high activity of the said catalyst composition resulting in high yield of the alpha olefins (>95 wt. %) as the product and significantly minimum polymer as by-product. The process provides higher yield of C6-C10 fraction with >60 wt. %.

19 Claims, No Drawings

PROCESS AND CATALYST COMPOSITION FOR PRODUCING LINEAR ALPHA OLEFINS IN HIGH YIELD BY ETHYLENE OLIGOMERIZATION

FIELD

The present disclosure relates to a process for preparation of linear alpha olefins in high yield. The process for producing linear alpha olefins in high yield is carried out by oligomerization of ethylene in the presence of a novel catalyst composition made of (i) Zirconium compound having formula ZrXm.nA, wherein X is halogen atom; m is an integer having value equal or less than 4, n is a number equal or less than 2, and A is selected from the group comprising of tetrahydrofuran, N,N-diisobutylacetamide or both (ii) an organoaluminum compound of the formula R1nAlY3-n, or Al2Y3R13, wherein R' represents an alkyl group having from 1 to 20 carbon atoms, Y represents Cl, Br or I, n is any number within the range 1≤n≤2, and (iii) at least one Lewis base selected from cyclic and acyclic ethers. The process is carried out in an organic solvent. The described process provides significantly high activity of the said catalyst composition resulting in high yield of the alpha olefins as the product and significantly minimum polymer as by-product.

BACKGROUND

Ethylene oligomerization process produces mixture of even carbon numbered olefins (from 4 to 20 plus carbon atoms) with terminal double bonds. Oligomerization process leads to the formation of undesired by-products such as internal olefins, branched olefins, and polymer together with the desired products. Therefore, the catalytic system and process conditions play an important role in ethylene oligomerization to get desired selectivity, purity of alpha olefins and product distribution. Some of the prior know processes and catalyst system as used for ethylene oligomerization are disclosed hereinbelow.

U.S. Pat. No. 4,486,615 discloses a binary composed of $ZrCl_4$ and Ethyl aluminum sesquichloride and a lewis base such as tertiary amine, an ether, a phosphine oxide, an alkyl phosphate, an aryl phosphate, a sulfoxide, which is added as a third component to increase the activity of binary system. However, lewis bases has reduced the catalyst activity with the enhancement of purity of linear alpha olefins by terminating the Friedel craft activity of the catalyst in ethylene oligomerization.

U.S. Pat. No. 4,783,573 discloses a catalytic system comprising of zirconium tetrachloride with aluminumsesquichloride and organic compounds containing heteroatom, such as alkyl disulphides, thioether, thiophene and primary amine are used as a lewis bases in dry benzene solvent. However, the catalyst selectivity is improved slightly towards C6-C14 but significant amount of olefin wax and polymer together with the linear alpha olefins are also observed due to the poor solubility of $ZrCl_4$ and severe reaction conditions of this process.

U.S. Pat. No. 5,260,500 discloses a catalyst composed of $ZrCl_4$ in combination of triethylamine & ethylaluminum sesquichloride using alcohol (methanol and/or ethanol) as a third component. This process is focused on production of high purity alpha olefins free of containment but high yield of C20+ fraction (14 to 30 wt %) is also obtained together with linear alpha olefins.

U.S. Pat. No. 5,345,023 discloses a catalyst obtained by mixing zirconium compound with the general formula $ZrX_xY_yO_z$ with organic compound from ketals and acetals group in combination of Diethyl aluminum chloride. These components are stirred under an argon atmosphere over a period of time to make active catalyst system and then evaluated for oligomerization of ethylene to light olefins (from C4 to C10). Said oligomerization catalyst shows low selectivity for C6-C10 fraction with formation of waxy solids of heavy oligomers which are eventually accumulate and causes reactor plugging and prevent a long production run.

U.S. Pat. Nos. 8,653,316 and 9,050,587 both disclose a zirconium based carboxylate complex of general formula $ZrCl_{4-m}(R^1COO)_m$ with an organoaluminum compound. Preferably diethyl aluminum chloride in combination of one electron donor or as a mixture of at least two electron donors to get synergistic effect on selectivity of catalyst system and purity of low molecular weight linear alpha-olefins. The purity of linear alpha olefins is improved with adverse effect on the catalyst activity in presence of electron donor at Al/Zr mole ratio of 17.5. The presence of high amount of undesired and problematic by-product such as wax and/or polymer with an increase in Al/Zr mole ratio not only lower the yield of low molecular weight oligomers, but also affect their purity. These waxes and/or polymer are required to be removed periodically from the reactor that reduces the working time of process equipment. Hence another disadvantage of the process is a low activity of the catalyst.

EP0241596B1 discloses a process for preparing a linear alpha-olefin having from 4 to 20 carbon atoms which comprises polymerizing ethylene or gas containing ethylene in the presence of a catalyst consisting of a zirconium halide, an organoaluminium compound and a Lewis base, and adding a catalyst deactivating agent to the resulting reaction mixture. However, alongwith linear alpha olefins, EP0241596B1 also produces small quantities of by-product wax.

WO2007090412 discloses a catalyst composition for the oligomerization of ethylene comprising at least one transition metal bisphenolate compound and at least one cocatalyst. The transition metal bisphenolate is a zirconium (IV) bisphenolate and the cocatalyst is an organoaluminium compound comprising diethyl aluminium chloride and/or ethyl aluminium sesquichloride. Further, the electron donor compound is selected from ethyl acetate, ethyl acetoacetate, ethyl benzoate, anisol, thiophene, tetrahydrofuran, cyclopentylamine and 2-pyrrolidone.

US20210178376 discloses a catalyst composition for ethylene oligomerization producing C4 to C16 linear oligomer product. The catalyst composition comprises zirconium amide compound, an organoaluminum compound and an additive. The zirconium amide compound is tetrachlorobis (tetrahydrofuran) zirconium and the substituted amide is N,N-diisobutylacetamide in a mole ratio of 0.1 to 5. The organoaluminum compound comprises diethylaluminum chloride or ethylaluminum sesquichloride; and the additive is selected from ethyl acetate, ethyl acetoacetate, ethyl benzoate, anisole, tetrahydrofuran, 1,2-dioxane, thiophen. The said catalyst compositions for ethylene oligomerization, wherein, the said composition is made of a transition metal compound and organoaluminum compound and a lewis base. The lewis base acts as an electron donor and enhances the selectivity of ethylene oligomerization via improved molecular weight control by terminating side reactions for the production of major portions of olefins other than linear alpha olefin products, particularly internal olefins but this in turn leads to reduction of the catalyst activity.

US20050070425 discloses catalytic composition for the selective oligomerization of ethylene and a process for preparing light linear (α-olefins). The catalyst composition comprises a compound of a transition metal M; wherein M comprises zirconium.

However, the known methods for ethylene oligomerization have many drawbacks like production of by-products such as wax and polymers along with low molecular weight oligomers. These undesired by-products lower the yield of low molecular weight oligomers and also affect their purity. Moreover, these waxes and/or polymer are required to be removed periodically from the reactor that reduces the working time of process equipment. Hence another disadvantage of the process is a low activity of the catalyst.

Accordingly, there is a need of a process and a catalyst composition for oligomerization of ethylene and to produce linear alpha olefins in high yield. Further, there is a need of a process and a catalyst composition to minimize the production of by-products such as wax and polymers during oligomerization of ethylene. Moreover, there is also a need of a process for oligomerization of ethylene with increased catalytic activity.

SUMMARY

The present invention describes a process and a novel catalyst composition for producing linear alpha olefins in high yield. The process for producing linear alpha olefins in high yield is carried out by oligomerization of ethylene in the presence of the catalyst composition which includes a Zirconium compound, an organoaluminum compound, and at least one Lewis base. The Zirconium compound having formula $ZrX_m \cdot nA$, wherein, X is a halogen atom, m is an integer having value equal or less than 4, n is a number equal or less than 2, and A is selected from the group comprising of tetrahydrofuran, N,N-diisobutylacetamide or both. The organoaluminum compound having formula $R^1{}_n AlY_{3-n}$, or the formula $Al_2Y_3R^1{}_3$, wherein, R1 represents an alkyl group having 1 to 20 carbon atoms, Y represents Cl, Br or I, n is any number within the range $1 \le n \le 2$, wherein, a mole ratio of aluminum to zirconium is from about 5:1 to about 100:1. The at least one Lewis base is selected from an ether, wherein, a mole ratio of zirconium to lewis base is from 1:10 to 1:50.

The Zirconium compound is tetrachlorobis(tetrahydrofuran) zirconium ($ZrCl_4 \cdot 2THF$), $ZrCl_4 \cdot 2(N,N-diisobutylacetamide)$ or a combination thereof.

The organoaluminum compound is selected from one of alkylaluminums, trialkenylaluminums, dialkylaluminum halides, alkylaluminum sesquihalides, dialkylaluminum hydrides, partially hydrogenated alkylaluminum, aluminoxane, diethylaluminum ethoxide, and a mixture thereof. The alkylaluminums is trialkylaluminum which is selected from triethylaluminum, triisopropylaluminum, triisobutylaluminum, tri-n-butylaluminum, tri-n-hexylaluminum, tri-n-octylaluminum. The trialkenylaluminums is triisoprenyl aluminum. The dialkylaluminum halides is selected from diethylaluminum chloride, dibutylaluminum chloride, diisobutylaluminum chloride and diethyl aluminum bromide. The alkylaluminum sesquihalides is selected from ethylaluminum sesquichloride, butylaluminum sesquichloride, ethylaluminum sesquibromide. The dialkylaluminum hydrides is selected from diethylaluminum hydride, dibutylaluminum hydride. The partially hydrogenated alkylaluminum is selected from ethylaluminum dihydride, propylaluminum dihydride. The aluminoxane is selected from methylaluminoxane, isobutylaluminoxane, tetraethylaluminoxane, tetraisobutylaluminoxane. The diethylaluminum ethoxide is selected from diethylaluminum chloride and ethylaluminum sesquichloride.

The catalyst composition as per the present disclosure have a mole ratio of aluminum to zirconium is from 10:1 to 70:1.

The lewis base is selected from cyclic and acyclic ethers, including, but not limiting to cycloaliphatic ethers, aromatic ethers, monoethers, diethers, tetraethers, polyethers such as diethyl ether, dibutyl ether, dipropyl ether, diisobutyl ether, diisopropyl ether, diphenyl ether, methyl butyl ether, methyl phenyl ether, dicyclohexyl ether, tert-butyl methyl ether, divinyl ether, 1,2 dimethoxy ethane, ethylene glycol dimethyl ether, furan, 2-methyl furan, tetrahydropyran, and mixtures thereof.

The catalyst composition as per the present disclosure have a mole ratio of zirconium to lewis base is from 1:10 to 1:50.

The present disclosure provides a process for preparing a catalyst composition used to produce linear alpha olefins by oligomerization of ethylene. The said process includes combining a zirconium compound, an organoaluminum compound, at least one Lewis base and an inert organic solvent. The zirconium compound having formula $ZrX_m \cdot nA$, wherein, X is a halogen atom, m is an integer having value equal or less than 4, n is a number equal or less than 2, and A is selected from the group comprising of tetrahydrofuran, N,N-diisobutylacetamide or both. The organoaluminum compound having formula $R^1{}_n AlY_{3-n}$, or the formula $Al_2Y_3R^1{}_3$, wherein, $R^1$ represents an alkyl group having 1 to 20 carbon atoms, Y represents Cl, Br or I, n is any number within the range $1 \le n \le 2$. The at least one Lewis base is selected from an ether. The inert organic solvent is selected from aromatic hydrocarbons substituted or unsubstituted with halogens, aliphatic paraffin hydrocarbons, alicyclic hydrocarbon compounds, halogenated alkanes, and a mixture thereof. The aromatic hydrocarbons are substituted or unsubstituted with halogens and are selected from toluene, benzene, xylene, chlorobenzene, dichlorobenzene, or chlorotoluene. The aliphatic paraffin hydrocarbons are selected from pentane, hexane, heptane, octane, nonane, decane. The alicyclic hydrocarbon compounds are selected from cyclohexane, or decahydronaphthalene. The halogenated alkanes are selected from dichloroethane, or dichlorobutane.

The present disclosure provides a process for producing linear alpha olefins by oligomerization of ethylene in the presence of the catalyst composition as disclosed hereinabove. The said process includes oligomerization of ethylene in an inert organic solvent in the presence of the said catalyst composition at a reaction temperature between 50° C. to 150° C. resulting >95 wt. % of alpha olefins and significantly minimum polymer/wax by-product. The reaction temperature is between 60° C. to 110° C.

The process provides linear oligomer product having broad weight percent distribution of C4-C24 carbon. The process provides >60 wt. % of C6-C10 fraction.

Objective

It is the primary objective of the present disclosure to provide a process and a catalyst composition for producing linear alpha olefins in high yield by oligomerization of ethylene.

It is a further objective of the present disclosure to provide a process for producing linear alpha olefins by carrying out the oligomerization of ethylene in the presence of a catalyst composition, wherein, the catalyst composition gives high activity despite using a lewis base.

It is a further objective of the present disclosure to provide a Lewis base selected from cyclic and acyclic ethers.

It is a further objective of the present disclosure to provide a catalyst composition made of (i) $ZrCl_4 \cdot 2THF$ or $ZrCl_4 \cdot 2$(N,N-diisobutylacetamide) or both (ii) ESCA or DEAC or ESCA/DEAC (iii) acyclic ethers, cyclic ethers or a combination thereof and an organic solvent.

This combination of Zr based catalyst with ether based lewis base provided ~3 times increase in catalyst activity as compared to commercially used acetate based lewis bases.

DESCRIPTION OF THE INVENTION

According to the main embodiment, the present disclosure provides a process and a catalyst composition for producing linear alpha olefins in high yield.

Specifically, the present disclosure provides a process for producing linear alpha olefins in high yield by oligomerization of ethylene in the presence of a catalyst composition made of (i) Zirconium compound having formula $ZrX_m \cdot nA$, wherein X is halogen atom; m is an integer having value equal or less than 4, n is a number equal or less than 2, and A is selected from the group comprising of tetrahydrofuran, N,N-diisobutylacetamide or both (ii) an organoaluminum compound of the formula $R^1{}_n AlY_{3-n}$, or $Al_2Y_3R^1{}_3$, wherein $R^1$ represents an alkyl group having from 1 to 20 carbon atoms, Y represents Cl, Br or I, n is any number within the range $1 \leq n \leq 2$, and (iii) at least one Lewis base selected from cyclic and acyclic ethers. Wherein, the Zirconium compound, the organoaluminum compound and at least one Lewis base all are combined in an inert organic solvent. The disclosed process provides significantly high activity of the said catalyst composition resulting in high yield of the alpha olefins as the product and significantly reduces production of polymer as the by-products.

In an embodiment, the zirconium compound having formula $ZrX_m \cdot nA$, wherein X is halogen atom, m is an integer having value equal or less than 4 and n is a number equal or less than 2 and A is selected from the group comprising of tetrahydrofuran, N,N-diisobutylacetamide or both.

The Zirconium compound is tetrachlorobis(tetrahydrofuran) zirconium ($ZrCl_4 \cdot 2THF$), $ZrCl_4 \cdot 2$(N,N-diisobutylacetamide) or a combination thereof. Preferably, the Zirconium compound is tetrachlorobis(tetrahydrofuran) zirconium, $ZrCl_4 \cdot 2THF$. In an embodiment, the zirconium compounds can be used in any mole ratio.

In an embodiment, the zirconium compound along with organoaluminum compound and Lewis base is used as catalyst composition for ethylene oligomerization providing high activity and producing linear oligomer product having broad weight percent distribution i.e. C4 to C24.

In an embodiment, the general formula of an organoaluminum compound is $R^1{}_n AlY_{3-n}$, or $Al_2Y_3R^1{}_3$, wherein $R^1$ represents an alkyl group having from 1 to 20 carbon atoms, Y represents Cl, Br or I, n is any number within the range $1 \leq n \leq 2$. The organoaluminum compound as disclosed herein include, not limiting, alkylaluminums such as trialkylaluminum such as triethylaluminum, triisopropylaluminum, tri-isobutylaluminum, tri-n-butylaluminum, tri-n-hexylaluminum, tri-n-octylaluminum; trialkenylaluminums such as triisoprenyl aluminum; dialkylaluminum halides such as diethylaluminum chloride, dibutylaluminum chloride, diisobutylaluminum chloride and diethyl aluminum bromide; alkylaluminum sesquihalides such as ethylaluminum sesquichloride, butylaluminum sesquichloride and ethylaluminum sesquibromide; dialkylaluminum hydrides such as diethylaluminum hydride and dibutylaluminum hydride; partially hydrogenated alkylaluminum such as ethylaluminum dihydride and propylaluminum dihydride and aluminoxane such as methylaluminoxane, isobutylaluminoxane, tetraethylaluminoxane and tetraisobutylaluminoxane; di ethyl aluminum ethoxide, preferably di ethyl aluminum chloride and ethylaluminum sesquichloride and their mixtures.

The mole ratio of aluminum to zirconium is from about 5:1 to about 100:1, preferably from about 10:1 to about 70:1.

In another embodiment of the present invention, lewis base is selected from cyclic and acyclic ethers, including, but not limiting to cycloaliphatic ethers, aromatic ethers, monoethers, diethers, tetraethers, polyethers such as diethyl ether, di-n-butyl ether, di-n-propyl ether, diisobutyl ether, diisopropyl ether, diphenyl ether, methyl butyl ether, methyl phenyl ether, dicyclohexyl ether, tert-butyl methyl ether, divinyl ether, 1,2 dimethoxy ethane, ethylene glycol dimethyl ether, furan, 2-methyl furan, tetrahydropyran, and mixtures thereof.

In one embodiment, mole ratio of zirconium to lewis base is from about 1:10 to about 1:30.

In one embodiment, the ethylene oligomeriation is carried out in an inert organic solvent. The inert organic solvent includes aromatic hydrocarbon solvents, unsubstituted or substituted with halogens, such as toluene, benzene, xylene, chlorobenzene, dichlorobenzene, chlorotoluene and the like, aliphatic paraffin hydrocarbons, such as pentane, hexane, heptane, octane, nonane, decane and the like, alicyclic hydrocarbon compounds, such as cyclohexane, decahydronaphthalene and the like, halogenated alkanes, such as dichloroethane, dichlorobutane and the like, and higher olefins of C6-C12 carbon chains. In one embodiment, a mixture of these solvents can also be used.

There are different ways to make a catalyst composition for ethylene oligomerization which are described hereinbelow.

I. Zirconium compound can be combined with at least one lewis base before combining it with alkylaluminum halide in a solvent preferably in an inert organic solvent. Inert organic solvent can be the same solvent, wherein, the oligomerization is carried out by utilizing this catalyst composition.

II. Zirconium compound can be combined with alkylaluminum halide in an inert organic solvent before adding at least one lewis base in it.

III. Solution of zirconium compound can be prepared in an inert organic solvent before adding into the solution of alkyl aluminum halide with at least one lewis base.

IV. Zirconium compound can be added as such into the solution of alkyl aluminum halide with at least one lewis base.

V. Zirconium compound, alkylaluminum halide and at least one lewis base can be combined in a suitable order in an inert organic solvent before introducing for ethylene oligomerization.

VI. Catalyst composition as disclosed herein can be formed in situ in the reactor by adding zirconium compound, alkylaluminum halide and at least one lewis base in an inert organic solvent.

However, according to present disclosure there is no particular limitation of the order of addition of the catalyst components. Preferably, the catalyst composition is prepared in a separate reaction vessel prior to their introduction into an oligomerization reactor. Contacting of catalyst component can be done under an inert atmosphere preferably nitrogen and/or argon. Catalyst composition can be prepared preferably at ambient temperature.

In an embodiment, the inventive catalyst composition for the oligomerization of ethylene produces linear alpha-olefins having a high degree of linearity, such as about 90 mole percent or greater within a desirable molecular weight range, i.e., oligomers of 4 to 24 carbon atoms.

According to the present invention, the catalyst composition can be utilized in the process for preparing linear alpha-olefins at a reaction temperature of about 50° C. to about 150° C., preferably between about 60° C. to about 110° C.

The catalyst composition of the present disclosure having zirconium compound and organoaluminum compound can be used without any lewis base for oligomerization of ethylene to produce linear low molecular weight alpha-olefins with broad weight percent distribution i.e. C4 to C24. Surprisingly, it was found that the said catalyst composition with at least one lewis base can further increase the catalyst activity and productivity and alter the product distribution particularly higher yield of C6 fraction with high purity of alpha-olefins and without formation of wax/polymer as a side product.

The catalyst composition utilized in this present disclosure provides several advantages. The zirconium compound is stable compound and is readily available. The compound is readily soluble when taken along the cocatalyst and lewis base. The catalyst provides high activity and productivity with linear oligomer product formation having broad weight percent distribution i.e., C4 to C24 particularly higher yield of C6 fraction with high purity of alpha-olefins without formation of wax/polymer as a by-product.

All the procedure was carried out under dry nitrogen atmosphere, using pre-dried reagents/solvents. All alkylaluminum compounds and solutions thereof were received from Gulbrandsen and were used as such.

EXAMPLE

Tetrachlorobis(tetrahydrofuran) zirconium was received from Sigma-Aldrich and was used as such. Tetrachlorobis(N,N-diisobutylacetamide)zirconium was prepared as reported in US20210178376.

Oligomerization of ethylene was performed as follows:

In a charging flask, equipped with nitrogen, 20 ml of dry toluene was added followed by addition of Zirconium catalyst. This clear homogenous mixture was stirred for 15 minutes and dissolution of the catalyst was observed. Then cocatalyst was added to the solution followed by addition of lewis base as the additive. At this point complete dissolution of catalyst was observed. This clear solution was charged into preconditioned reactor at 30° C. having dry toluene. The oligomerization was conducted at 80° C. and 35 bar ethylene pressure for 60 minutes. After the retrieval of clear liquid, it was treated with 10 ml methanol for quenching the catalyst system. There was no wax formation as well as polymer formation and if polymer was detected, it was only in traces.

A sample of liquid product was analyzed by gas chromatography (GC-FID) to determine the quantity & distribution of ethylene and higher oligomers.

The following examples are included herein for illustrative purposes only. Those skilled in the art will appreciate that many modifications may be made in the invention without changing the essence of invention.

Abbreviations

1. EASC=ethylene aluminum sesquichloride
2. DEAC=diethylaluminum chloride
3. DEE=diethylether
4. DPE=di-n-propylether
5. DBE=di-n-butylether
6. EA=ethyl acetate
7. DiPE=di-iso-propylether
8. BPE=butylphenylether
9. 2MF=2-methyl furan
10. EG=monoethylene glycol
11. $ZrCl_4 \cdot 2THF$=tetrachlorobis(tetrahydrofuran) zirconium=ZrT
12. $ZrCl_4 \cdot 2(N, N\text{-diisobutylacetamide})$=Tetrachlorobis(N,N-diisobutylacetamide)zirconium=ZrN Further, below tables (1-4) depict Ethylene oligomerization using different conditions and details of the conditions is provided in the tables (1-4) as mentioned hereinbelow.

TABLE 1

Working examples of using different cyclic and acyclic ethers as additives for oligomerization of ethylene using EASC as cocatalyst, Al/Zr (mol) = 17.5 and Zr/additive (mol) = 30

| S. No. | Catalyst | Additive | Productivity (kg LAO/g Zr) | Distribution of α-olefins (wt %) | | | | α-olefins (wt %) |
|---|---|---|---|---|---|---|---|---|
| | | | | C4 | C6-C10 | C12-C18 | C20+ | |
| OLM#1 | ZrT | EA | 2.2 | 32.3 | 58.2 | 9.4 | 0.03 | >90 |
| OLM#2 | ZrN | | 3.4 | 38.7 | 54.8 | 6.4 | 0.1 | >96 |
| OLM#3 | ZrT/ZrN (1:1 mole ratio) | | 3.1 | 36.3 | 57.2 | 6.4 | 0.1 | >92 |
| OLM#4 | ZrT | DEE | 14.0 | 19.8 | 60.9 | 19.2 | 0.1 | >96 |
| OLM#5 | ZrN | | 13.0 | 20.4 | 61.2 | 18.2 | 0.2 | >96 |
| OLM#6 | ZrT/ZrN (1:1 mole ratio) | | 15.0 | 19.5 | 62.0 | 18.4 | 0.1 | >96 |
| OLM#7 | ZrT | DBE | 14.3 | 17.4 | 64.6 | 17.9 | 0.1 | >96 |
| OLM#8 | ZrN | | 13.9 | 19.7 | 64.9 | 15.3 | 0.1 | >95 |
| OLM#9 | ZrT/ZrN (1:1 mole ratio) | | 16.1 | 17.5 | 65.1 | 17.3 | 0.1 | >96 |
| OLM#10 | ZrT | DiPE | 13.9 | 13.9 | 67.1 | 18.9 | 0.1 | >97 |
| OLM#11 | ZrN | | 14.3 | 15.7 | 66.9 | 17.3 | 0.1 | >96 |
| OLM#12 | ZrT/ZrN (1:1 mole ratio) | | 15.0 | 15.0 | 67.6 | 17.3 | 0.1 | >96 |
| OLM#13 | ZrT | BPE | 15.0 | 16.8 | 65.7 | 17.4 | 0.1 | >95 |
| OLM#14 | ZrN | | 14.7 | 18.2 | 64.9 | 16.8 | 0.1 | >97 |

TABLE 1-continued

Working examples of using different cyclic and acyclic ethers as additives for oligomerization of ethylene using EASC as cocatalyst, Al/Zr (mol) = 17.5 and Zr/additive (mol) = 30

| S. No. | Catalyst | Additive | Productivity (kg LAO/g Zr) | Distribution of α-olefins (wt %) C4 | C6-C10 | C12-C18 | C20+ | α-olefins (wt %) |
|---|---|---|---|---|---|---|---|---|
| OLM#15 | ZrT/ZrN (1:1 mole ratio) |  | 16.7 | 16.6 | 65.8 | 17.5 | 0.1 | >96 |
| OLM#16 | ZrT | 2MF | 13.1 | 16.7 | 66.3 | 16.9 | 0.1 | >96 |
| OLM#17 | ZrN |  | 13.2 | 17.4 | 65.2 | 17.3 | 0.1 | >96 |
| OLM#18 | ZrT/ZrN (1:1 mole ratio) |  | 14.0 | 14.7 | 67.1 | 18.1 | 0.1 | >97 |
| OLM#19 | ZrT | EG | 14.7 | 14.5 | 66.8 | 18.6 | 0.1 | >96 |
| OLM#20 | ZrN |  | 13.9 | 16.4 | 67.2 | 16.3 | 0.1 | >96 |
| OLM#21 | ZrT/ZrN (1:1 mole ratio) |  | 17.0 | 12.7 | 68.3 | 18.9 | 0.1 | >97 |

TABLE 2

Working examples of using different cocatalyst for oligomerization of ethylene using DBE as additive, Al/Zr (mol) = 17.5 and Zr/additive (mol) = 30

| S. No. | Catalyst | Cocatalyst | Productivity (kg LAO/g Zr) | Distribution of α-olefins (wt %) C4 | C6-C10 | C12-C18 | C20+ | α-olefins (wt %) |
|---|---|---|---|---|---|---|---|---|
| OLM#7 | ZrT | EASC | 14.3 | 17.4 | 64.6 | 17.9 | 0.1 | >96 |
| OLM#8 | ZrN |  | 13.9 | 19.7 | 64.9 | 15.3 | 0.1 | >95 |
| OLM#9 | ZrT/ZrN (1:1 mole ratio) |  | 16.1 | 17.5 | 65.1 | 17.3 | 0.1 | >96 |
| OLM#22 | ZrT | DEAC | 15.6 | 11.3 | 67.6 | 20.9 | 0.2 | >96 |
| OLM#23 | ZrN |  | 14.5 | 12.7 | 67.9 | 19.3 | 0.1 | >96 |
| OLM#24 | ZrT/ZrN (1:1 mole ratio) |  | 17.1 | 11.2 | 67.4 | 21.3 | 0.1 | >96 |
| OLM#25 | ZrT | EASC/DEAC (1:1 mol ratio) | 18.6 | 13.6 | 65.8 | 20.5 | 0.1 | >96 |
| OLM#26 | ZrN |  | 17.8 | 16.2 | 64.0 | 19.7 | 0.1 | >96 |
| OLM#27 | ZrT/ZrN (1:1 mole ratio) |  | 18.7 | 15.8 | 64.3 | 19.8 | 0.1 | >96 |

TABLE 3

Working examples of using different mol ratios of alkyl aluminums for oligomerization of ethylene using EASC as cocatayst, DBE as additive and Zr/additive (mol) = 30

| S. No. | Catalyst | Al/Zr | Productivity (kg LAO/g Zr) | Distribution of α-olefins (wt %) C4 | C6-C10 | C12-C18 | C20+ | α-olefins (wt %) |
|---|---|---|---|---|---|---|---|---|
| OLM#7 | ZrT | 17.5 | 14.3 | 17.4 | 64.6 | 17.9 | 0.1 | >96 |
| OLM#8 | ZrN |  | 13.9 | 19.7 | 64.9 | 15.3 | 0.1 | >95 |
| OLM#9 | ZrT/ZrN (1:1 mole ratio) |  | 16.1 | 17.5 | 65.1 | 17.3 | 0.1 | >96 |
| OLM#28 | ZrT | 35 | 17.3 | 15.6 | 66.1 | 18.2 | 0.1 | >96 |
| OLM#29 | ZrN |  | 14.9 | 15.3 | 65.8 | 18.8 | 0.1 | >96 |
| OLM#30 | ZrT/ZrN (1:1 mole ratio) |  | 17.5 | 15.5 | 65.7 | 18.7 | 0.1 | >96 |
| OLM#31 | ZrT | 5 | 0.8 | 80.2 | 12.6 | 7.1 | 0.1 | >75 |
| OLM#32 | ZrN |  | 0.2 | 45.6 | 34.7 | 19.6 | 0.1 | >75 |
| OLM#33 | ZrT/ZrN (1:1 mole ratio) |  | 0.6 | 77.3 | 13.5 | 9.1 | 0.1 | >75 |
| OLM#34 | ZrT | 65 | 18.6 | 14.9 | 64.5 | 20.3 | 0.3 | >95 |
| OLM#35 | ZrN |  | 18.9 | 12.9 | 65.2 | 21.5 | 0.4 | >95 |
| OLM#36 | ZrT/ZrN (1:1 mole ratio) |  | 19.1 | 12.4 | 65.6 | 21.5 | 0.5 | >95 |
| OLM#37 | ZrT | 200 | No oligomerization | — | — | — | — | — |
| OLM#38 | ZrN |  |  | — | — | — | — | — |
| OLM#39 | ZrT/ZrN (1:1 mole ratio) |  |  | — | — | — | — | — |

TABLE 4

Working examples of using different mol ratio of DBE for oligomerization of ethylene using EASC as cocatalyst and Al/Zr mol ratio as 17.5

| S. No. | Catalyst | Zr/Additive mol ratio | Productivity (kg LAO/g Zr) | Distribution of α-olefins (wt %) | | | | α-olefins (wt %) |
|---|---|---|---|---|---|---|---|---|
| | | | | C4 | C6-C10 | C12-C18 | C20+ | |
| OLM#7 | ZrT | 30 | 14.3 | 17.4 | 64.6 | 17.9 | 0.1 | >96 |
| OLM#8 | ZrN | | 13.9 | 19.7 | 64.9 | 15.3 | 0.1 | >95 |
| OLM#9 | ZrT/ZrN | | 16.1 | 17.5 | 65.1 | 17.3 | 0.1 | >96 |
| | (1:1 mole ratio) | | | | | | | |
| OLM#40 | ZrT | 20 | 14.1 | 16.2 | 64.1 | 19.6 | 0.1 | >96 |
| OLM#41 | ZrN | | 14.2 | 16.8 | 63.4 | 19.7 | 0.1 | >96 |
| OLM#42 | ZrT/ZrN | | 15.2 | 16.5 | 64.0 | 19.4 | 0.1 | >96 |
| | (1:1 mole ratio) | | | | | | | |
| OLM#43 | ZrT | 10 | 13.9 | 16.2 | 63.2 | 20.5 | 0.1 | >96 |
| OLM#44 | ZrN | | 14.1 | 16.3 | 64.2 | 19.4 | 0.1 | >96 |
| OLM#45 | ZrT/ZrN | | 15.0 | 16.1 | 64.2 | 19.6 | 0.1 | >96 |
| | (1:1 mole ratio) | | | | | | | |

We claim:

1. A catalyst composition for producing linear alpha olefins by oligomerization of ethylene, the catalyst composition consisting of:
   (i) a zirconium compound, wherein the zirconium compound is combination of tetrachlorobis (tetrahydrofuran) zirconium (ZrCl$_4$·2THF), ZrCl$_4$·2 (N,N-diisobutylacetamide) wherein ZrCl$_4$·2THF and ZrCl$_4$·2 (N,N-diisobutylacetamide) are in a mole ratio of 1:1;
   (ii) an organoaluminum compound having a formula R$^1_n$AlY$_{3-n}$, or a formula Al$_2$Y$_3$R$^1_3$, wherein R$^1$ represents an alkyl group having 1 to 20 carbon atoms, Y represents Cl, Br, or I, n is a number 1≤n≤2; and
   iii) at least one Lewis base, wherein the Lewis base is selected from a group consisting of cyclic and acyclic ethers.

2. The catalyst composition as claimed in claim 1, wherein the organoaluminum compound is selected from the group consisting of diethylaluminum chloride, ethylaluminum sesquichloride and a mixture thereof.

3. The catalyst composition as claimed in claim 1, wherein aluminum present in the organoaluminum compound and zirconium present in the zirconium compound are in a mole ratio in a range of 10:1 to 70:1.

4. The catalyst composition as claimed in claim 1, wherein the cyclic and acyclic ethers are at least one of cycloaliphatic ethers, aromatic ethers, monoethers, diethers, tetraethers and polyethers.

5. The catalyst composition as claimed in claim 1, wherein the cyclic and acyclic ethers are selected from the group consisting of diethyl ether, di-n-butyl ether, di-n-propyl ether, diisobutyl ether, diisopropyl ether, diphenyl ether, methyl butyl ether, methyl phenyl ether, dicyclohexyl ether, tert-butyl methyl ether, divinyl ether, 1,2 dimethoxy ethane, ethylene glycol dimethyl ether, and a mixture thereof.

6. The catalyst composition as claimed in claim 1, wherein the zirconium in the zirconium compound and the Lewis base are in a mole ratio in a range of 1:10 to 1:30.

7. A process for preparing a catalyst composition to produce linear alpha olefins by oligomerization of ethylene, the process comprising:
   mixing a zirconium compound, an organoaluminum compound, at least one Lewis base and an inert organic solvent in a reactor; and
   forming the catalyst composition in situ in the reactor, wherein the zirconium compound has a formula ZrX$_m$·nA, wherein X is a halogen atom, m is an integer having a value equal to or less than 4, n is a number equal to or less than 2, and A is selected from the group consisting of tetrahydrofuran, N,N-diisobutylacetamide and a combination thereof,
   wherein the organoaluminum compound has a formula R$^1_n$AlY$_{3-n}$, or a formula Al$_2$Y$_3$R$^1_3$, wherein R$^1$ represents an alkyl group having 1 to 20 carbon atoms, Y represents Cl, Br or I, n is a number 1≤n≤2, and
   wherein the Lewis base is selected from a group consisting of cyclic and acyclic ethers.

8. The process as claimed in claim 7, wherein the inert organic solvent is selected from the group consisting of unsubstituted aromatic hydrocarbons, aromatic hydrocarbons substituted with halogens, aliphatic paraffin hydrocarbons, alicyclic hydrocarbon compounds, halogenated alkanes, and a mixture thereof.

9. A process for producing linear alpha olefins by oligomerization of ethylene in the presence of a catalyst composition, the process consisting of:
   preparing a catalyst composition in a reactor at ambient temperature;
   charging ethylene into an oligomerization reactor;
   charging the catalyst composition into the oligomerization reactor under an inert atmosphere at a reaction temperature between 50° C. to 150° C.; and
   producing about 95 wt. % of linear alpha olefins and traces of polymer by-product, wherein the catalyst composition consists of:
   a combination of ZrCl$_4$·2THF and ZrCl$_4$·2 (N,N-diisobutylacetamide) wherein ZrCl$_4$·2THF and ZrCl$_4$·2 (N,N-diisobutylacetamide) are in a mole ratio of 1:1;
   an organoaluminum compound having a formula R$^1_n$AlY$_{3-n}$, or a formula Al$_2$Y$_3$R$^1_3$, wherein R$^1$ represents an alkyl group having 1 to 20 carbon atoms, Y represents Cl, Br, or I, n is a number 1≤n≤2; and
   at least one Lewis base, wherein the Lewis base is selected from a group consisting of cyclic and acyclic ethers.

10. The process as claimed in claim 9, wherein the linear alpha olefins have a weight percent distribution of C4-C24 carbon.

11. The process as claimed in claim 9, wherein the linear alpha olefins have greater than 60 wt. % of C6-C10 fraction.

12. The process as claimed in claim 9, wherein the reaction temperature is between 60° C. to 110° C.

13. The process as claimed in claim 9, wherein preparing the catalyst composition in the reactor at ambient temperature comprises:
   mixing a zirconium compound, an organoaluminum compound, at least one Lewis base and an inert organic solvent in the reactor; and
   forming the catalyst composition in situ in the reactor.

14. The process as claimed in claim 13, wherein the inert organic solvent is selected from the group consisting of unsubstituted aromatic hydrocarbons, aromatic hydrocarbons substituted with halogens, aliphatic paraffin hydrocarbons, alicyclic hydrocarbon compounds, halogenated alkanes, and a mixture thereof.

15. The process as claimed in claim 14, wherein the substituted aromatic hydrocarbons are selected from the group consisting of toluene, benzene, xylene, chlorobenzene, dichlorobenzene, and chlorotoluene.

16. The process as claimed in claim 14, wherein the aliphatic paraffin hydrocarbons are selected from the group consisting of pentane, hexane, heptane, octane, nonane, and decane.

17. The process as claimed in claim 14, wherein the alicyclic hydrocarbon compounds are cyclohexane, or decahydronaphthalene.

18. The process as claimed in claim 14, wherein the halogenated alkanes are dichloroethane, or dichlorobutane.

19. The process as claimed in claim 9, wherein the inert atmosphere is provided by nitrogen or argon.

* * * * *